(12) United States Patent
Jackson

(10) Patent No.: US 6,179,802 B1
(45) Date of Patent: Jan. 30, 2001

(54) NITROCELLULOSE COATED TAMPON APPLICATOR HAVING A PIERCE-THROUGH FINGERGRIP

(75) Inventor: Dane R. Jackson, Bloomingdale, NJ (US)

(73) Assignee: Playtex Products, Inc., Westport, CT (US)

(*) Notice: Under 35 U.S.C. 154(b), the term of this patent shall be extended for 0 days.

(21) Appl. No.: 09/354,692

(22) Filed: Jul. 16, 1999

Related U.S. Application Data

(63) Continuation-in-part of application No. 09/041,521, filed on Mar. 12, 1998, now Pat. No. 5,931,803.

(51) Int. Cl.[7] .................................................. A61F 13/20
(52) U.S. Cl. ............................................................ 604/15
(58) Field of Search ...................... 604/11–18, 285–288, 604/904, 57–60, 311

(56) References Cited

U.S. PATENT DOCUMENTS

| | | | |
|---|---|---|---|
| 2,587,717 | * | 3/1952 | Fourness ................................ 604/14 |
| 5,346,468 | * | 9/1994 | Campion et al. ....................... 604/13 |
| 5,348,534 | * | 9/1994 | Tomaszewski et al. ............... 604/14 |

\* cited by examiner

Primary Examiner—Dennis Ruhl
(74) Attorney, Agent, or Firm—Ohlandt, Greeley, Ruggiero, & Perle, LLP

(57) ABSTRACT

An applicator is disclosed that is adapted for insertion into a body cavity. The applicator has an outer surface that is coated with a nitrocellulose layer and an pierce-through fingergrip area. Also disclosed is a method for forming such an applicator, and tampon assemblies constructed with same.

19 Claims, 1 Drawing Sheet

NITROCELLULOSE COATED TAMPON APPLICATOR HAVING A PIERCE-THROUGH FINGERGRIP

RELATED APPLICATION

This application is a continuation in part of U.S. application Ser. No. 09/041,521 filed Mar. 12, 1998 and now U.S. Pat. No. 5,931,803.

BACKGROUND OF THE INVENTION

1. Field of the Invention

The present invention relates to a cardboard tampon applicator. More particularly, the present invention relates to a cardboard or paper laminate tampon applicator that is coated with a nitrocellulose coating. The applicator preferably has a pierce-through or perforation type fingergrip. The nitrocellulose coated cardboard tampon applicator of the present invention can be formed inexpensively, and will have a high degree of gloss and slip for easier insertion, as well as improved cross-sectional circularity for reduced ejection force.

2. Description of the Prior Art

Tampon applicators are generally formed either from a molded thermoplastic material, such as plastic, or a paper laminate, such as cardboard or paperboard.

It is desired that tampon applicators have a generally circular cross-sectional shape. Maintaining this generally circular shape has been found to reduce the force needed to eject the tampon pledget from the applicator, thus making the tampon applicator more acceptable to the consumer. Well known methods exist to produce molded plastic applicators with regular and consistent cross-section. Moreover, such molded plastic applicators can be formed with a high degree of surface smoothness, which results in increased comfort during insertion of the tampon. However, plastic tampon applicators are neither water dispersible nor biodegradable in any practical sense, unless certain expensive plastics are used. Yet in an ecology-minded society, biodegradability is desirable.

To obtain a biodegradable tampon applicator, paper laminates, such as cardboard, are preferred since such applicators delaminate upon saturation with water. This delamination facilitates the process of biodegradation. To approximate the aesthetics and ease of insertion of plastic tampon applicators, paper applicators are conventionally formed with an outer film layer that is bonded to the applicator by adhesive or the like. However, it is difficult to manufacture a film laminated paper applicator with a perfectly circular cross-section, and the degree of circularity of the laminated paper applicator has been found to degrade further during the tube-forming heating stage of the manufacturing process. Moreover, the applicator is enhanced by including a fingergrip on the barrel of the applicator. However, it has been found to be difficult to produce a fingergrip that is sufficiently grippable.

Alternatively, some commercially available cardboard applicators have a coating that is applied as a liquid and subsequently solidifies on the applicator. For example, liquid wax coatings are inexpensive to apply, and will not degrade the circularity of the tampon applicator during the manufacturing process. However, such liquid wax-coated tampon applicators do not have sufficient surface smoothness and, therefore, do not provide the desired insertion comfort and reduced ejection force.

A polyester film coating that has been used on commercially available tampon applicators has been found to shrink during the heating cycle of the applicator manufacturing process, causing distortion of the applicator's shape. As discussed above, this distortion of the applicator's circular cross-section increases the ejection force required. Cellophane film, also known in the art for use on paper tampon applicators, similarly shrinks due to the evaporation of water absorbed from the adhesive used to apply it to the applicator. Furthermore, the hydrophilic cellophane coating on applicators provide poor insertion comfort. Consequently, cellophane is usually coated with a water resistant coating to improve insertion comfort, discussed further below. Coated cellophane is relatively expensive because it requires a supplemental coating on top of a base layer. In addition, the use of such a coating can require special handling and disposal procedures, all of which further raise manufacturing costs.

Coated paper laminate applicators are known in the art. For example, U.S. Pat. No. 4,412,833 to Weigner et al. is directed to an applicator formed of a high-gloss paper that can be coated with a degradable, dispersible or water soluble polymer, such as a modified polyethylene, polypropylene, polyvinylidene chloride or polyvinyl alcohol.

U.S. Pat. No. 4,508,531 to Whitehead provides an applicator with a heat-sensitive coating, such as a polyolefin (e.g., polyethylene or polypropylene) or a heat sensitive adhesive.

U.S. Pat. No. 4,622,030 to Shelton provides a thermoplastic coated paper tube. A film layer on a paper laminate tampon applicator is disclosed in U.S. Pat. No. 5,346,468 to Campion et al. This paper laminate tampon applicator has a thermoset polymer film layer adhered to the outer surface of the cardboard applicator. Preferably, this polymer film layer is a cellophane layer. A film layer of a thermoplastic polymer such as polyethylene, polyester, polypropylene, polycaprolactone or ethylene vinyl acetate can allegedly be used in place of cellophane.

As an ancillary component, this patent discloses a water resistant coating for use on top of the cellophane layer. This water resistant coating may include polyvinylidine chloride or nitrocellulose. The patent further discloses that a nitrocellulose-coated cellophane sheet is commercially available from Flexel. However, the patent does not suggest the use of a nitrocellulose coating directly on a cardboard tampon applicator. Moreover, it does not suggest a nitrocellulose-based coating containing other components.

Thus, a nitrocellulose coating is known for use in providing water-resistance to a cellophane film layer applied to a tampon applicator. However, no applicator is known that has a nitrocellulose coating applied to the outer paper lamina. Moreover, even the known cellophane film-coated applicator does not have the multiple puncture fingergrip of the present applicator and may not appreciate the significant circularity improvement provided by a nitrocellulose coating applied directly to the outer paper lamina of the applicator.

Thus, the liquid and film coatings described above have not enabled the combination of formation of the desired glossy finish, retention of applicator circularity, desired insertion comfort and desired fingergrip, and sufficient biodegradability. Further, many prior art liquid coatings and compound coatings are more expensive to use.

The present invention is directed to applying a liquid nitrocellulose coat on the surface of the paper laminate applicator, and thereafter optionally forming a multiple puncture fingergrip on the applicator. The applicator thus formed has the desired high gloss finish and maintains the improved degree of circularity of the applicator, while still permitting water dispersibility and biodegradability. The liquid coating of the present invention provides for the formation of the multiple puncture fingergrip, is inexpensive to apply, and does not require the use of organic solvents in the manufacturing process.

SUMMARY OF THE INVENTION

It is an object of the present invention to provide a coated paper laminate or cardboard tampon applicator that can maintain a preferred degree of circularity, leading to reduced ejection forces.

It is another object of the present invention to provide such a coated applicator having a multiple puncture fingergrip that provides a high degree of grippability.

It is yet another object of the present invention to provide such a coated applicator that can be inexpensively manufactured, without the need for multiple coating layers or laminae.

It is yet another object of the present invention to provide such a coated applicator that is water dispersible and where the coated layer will not prohibit the saturation and water dispersibility of the underlying substrate.

It is still yet another object of the present invention to provide such a coated applicator that can be inserted comfortably.

To accomplish the forgoing objects and advantages, the present invention, in brief summary, is a paper laminate or cardboard tampon applicator, having a multiple puncture fingergrip, that has an exterior surface coated directly with a nitrocellulose coating. The nitrocellulose coating can be applied to the applicator barrel, the plunger, or both. Although described in terms of a tampon applicator, the present invention is equally useful in devices for the application of suppositories, creams, or the like to the vaginal area or other body cavities.

DETAILED DESCRIPTION OF THE INVENTION

The present invention provides a nitrocellulose coating on a tampon applicator or similar device formed from a paper laminate such as cardboard. The paper laminate applicator, which is known in the prior art, can be spirally or convolutely wound. Typically, the applicator is formed by winding layers of a paper based material that can be paper or a paper-like material, such as cardboard, around a shaped mandrel, with each layer bonded, such as by glue or adhesive, to an adjacent layer.

Figure 1:
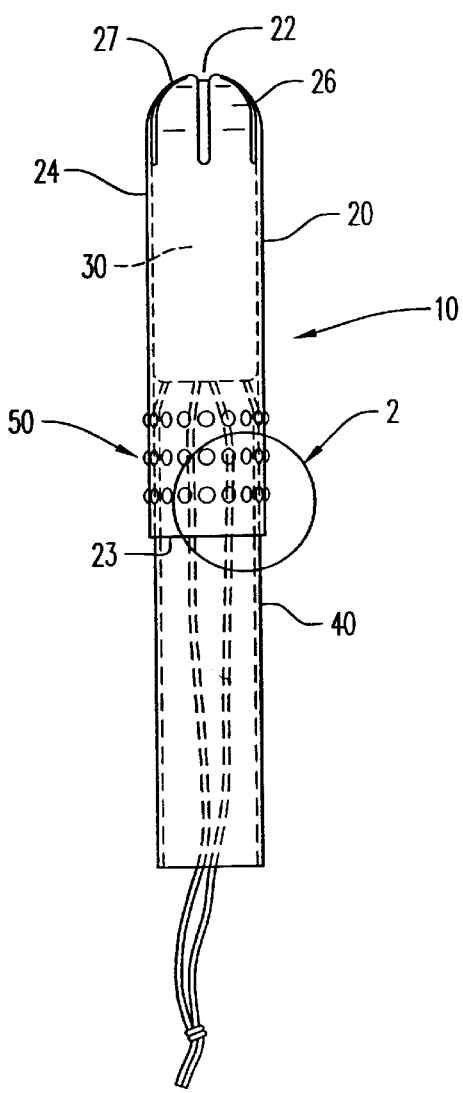
FIG. 1 is a side elevational view of a preferred tampon applicator including the applicator barrel of the invention.

Referring to the drawings and, in particular, FIG. 1, there is provided a tampon applicator generally represented by reference numeral 10. The tampon applicator 10 has an applicator barrel 20 having a forward end 22 and a rear end 23. The applicator barrel 20 has an exterior layer or lamina 24 formed of a nitrocellulose coated paper-based product. Alternatively, the exterior layer of applicator barrel 20 can be coated with nitrocellulose after the barrel is formed. Within applicator barrel 20, there can be positioned a tampon pledget 30. A plunger 40 is provided, which slidingly engages rear end 23 of applicator barrel 20. The plunger 40 is adapted to contact tampon pledget 30 to expel the tampon pledget through forward end 22 of applicator barrel 20. Preferably, forward end 22 is constructed from a plurality of petals 26 collectively shaped to form a dome 27. The applicator barrel 20 is preferably provided with a fingergrip area 50.

Figure 2:
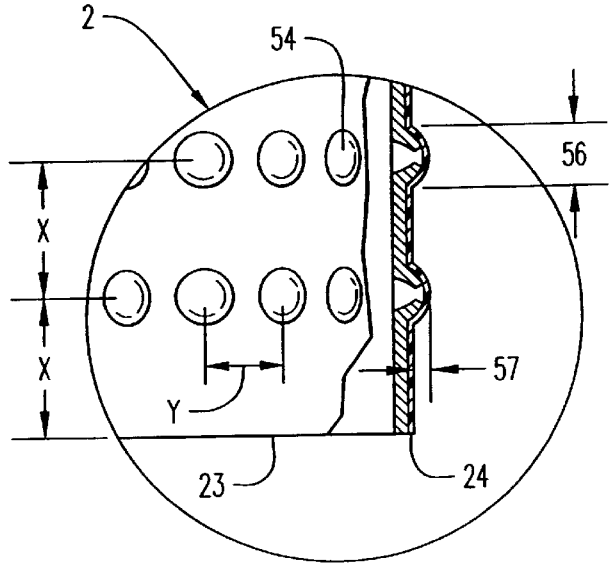
FIG. 2 is an enlarged view of region 2 of FIG. 1 showing an enlarged view of fingergrip area of the applicator barrel shown in FIG. 1.

The details of fingergrip area or fingergrip 50 are shown in FIG. 2. Generally, fingergrip area 50 is provided proximal rear end 23 of applicator barrel 20 and is provided with a three-dimensional texture by a plurality of outward-extending deformations 54. Although deformations 54 can be formed in any pattern, or randomly, within fingergrip area 50, it is convenient to form the deformations in rows positioned parallel to rear end 23 and spaced apart from each other by a row spacing distance X. This row spacing distance X is preferably about 0.25 inches. Further, the deformations 54 in any given row will be spaced from each other by a deformation spacing distance Y. This deformation spacing distance Y is preferably about 0.11 inches. Each deformation 54 can have a preferred base deformation width 56 of about 0.0045 inches to about 0.080 inches, and a preferred average deformation height 57 of about 0.016 inches. At the apex or point of each deformation 54, the paper-based layer of the applicator barrel 20 will be pierced through. However, the nitrocellulose layer, denoted in FIG. 2 as element 24, is typically not pierced and remains deformed but intact (See FIG. 1).

To form such a fingergrip, multiple deformations 54 of the nitrocellulose-coated laminate sheet are preferably made from the interior side. It is preferred that the deformations 54 puncture through the paper, but not through the moderately resilient film or layer formed by the nitrocellulose coating 24. The nitrocellulose coating 24 provides for the formation of superior fingergrips using this piercing technology since it permits the ready piercing or puncturing of the entire paper, but not piercing of the coating. In contrast, polyester coatings are so tough that the coated paper laminate sheets cannot be easily deformed and optimum deformation height cannot be easily achieved. Thus, the nitrocellulose coated applicators provide superior fingergrips compared to polyester coated applicators when the piercing technology is employed.

The present cardboard applicator 10 is preferably formed by a process that includes the application of the nitrocellulose coating to a first side or surface of a first sheet that will form the outer surface of the cardboard applicator barrel, plunger, or both. Thereafter, the coated first sheet is adhered to a second sheet to form a laminated structure that is, in turn, formed into the body of the tampon applicator. That first surface will form the exterior or outer surface of the formed cardboard applicator.

The nitrocellulose coating is preferably applied onto that first surface as a liquid by conventional liquid application devices and allowed to dry. This process forms a high gloss, hardened nitrocellulose coat. Thereafter, an aqueous adhesive is preferably applied to a second side or surface of the first sheet, and under nip roll pressure, the first sheet is bonded to the second sheet, which in turn may be bonded to a third or more sheets, to form the laminated structure. According to this preferred method, the laminate structure is then cut into small substrates or blanks. The substrates or blanks are subsequently wound (preferably convolutely) around a mandrel and heated to form the applicator. Either the blanks or the formed applicators are pierced to form the fingergrip area. As discussed above, the nitrocellulose coating can also be applied to the pre-formed applicator.

The preferred nitrocellulose coating contains adjuvant ingredients in addition to the nitrocellulose component. The most preferred nitrocellulose coating for use in the present invention is commercially available from Scholle Corporation of College Park, Georgia as Scholle 5088 Special Purpose Coating.

The Scholle 5088 Special Purpose Coating contains in its liquid form, n-propyl acetate, nitrocellulose, isopropanol, castor oil U.S.P., and synthetic paraffin wax. The relative weight percents of these ingredients are maintained by the supplier as proprietary information. When this preferred coating is applied to the outer paper layer of a cardboard tampon applicator, the solvents evaporate, leaving a dry film containing nitrocellulose, castor oil U.S.P. and synthetic paraffin wax. Other coatings containing nitrocellulose, exclusively or in combination with other coating aids, are also within the purview of the present invention.

The nitrocellulose coating is preferably applied to the first sheet in an amount at least about 2 pounds per ream. A ream contains approximately 3,000 square feet of paper. More preferably, the nitrocellulose coating will be applied in an amount about 2 to about 6 pounds per ream. The application of a greater amount of the nitrocellulose coating leads to a smoother and glossier finish.

It has been found that the heating process typically used to form applicator 10 causes shrinkage of the known nitrocellulose over cellophane film and polyester film coated cardboard applicators. However, the nitrocellulose coating, when used alone, does not shrink. Thus, the nitrocellulose coated cardboard applicator 10 will not cause distortions in the cross-section of the applicator or in the shape and conformation of the applicator petals. This improved degree of circularity has been found to reduce the amount of force required to eject the pledget from the applicator and to prevent the plunger from jamming in the applicator barrel.

The degree of circularity can be defined by optically measuring the major and minor diameters of the applicator and determining the perimeter thereof. The major diameter is then compared to the diameter of a perfect circle having the same perimeter as the measured applicator. The result is expressed in terms of % ovality, which is defined as follows:

% ovality=((Major diameter of the applicator/Diameter of a perfect circle of the same perimeter)−1)×100

The nitrocellulose coated applicator of the present invention have a lower degree of ovality, that is each applicator is more circular, than polyester film coated applicators.

In addition, the nitrocellulose coating is more water dispersible than prior polyester film coatings and nitrocellulose over cellophane coatings. Therefore, when flushed down a toilet, the nitrocellulose coating will disperse with only mild agitation, and will not separate from the applicator as a self-standing film. In contrast to polyester and cellulose, nitrocellulose will not delaminate from the applicator paper. Moreover, the nitrocellulose coating allows for the formation of an improved multiple puncture fingergrip.

The resultant coated tampon applicator will have a smooth, hydrophobic surface that provides for comfortable insertion of the applicator. It also is believed that the nitrocellulose coated applicator has a superior appearance and feel. Moreover, the nitrocellulose coating on the multiple puncture fingergrip 50 of the present applicator 10 provides a superior fingergrip.

When the plunger is also coated with nitrocellulose, the ejection properties of the tampon are further improved. Because the nitrocellulose coating is very hydrophobic, it resists the swelling and/or raising of pulp fibers on the surface of the plunger in situations where the surface gets wet from, for example, wet hands or menses. Reduced swelling of the plunger avoids ejection force problems due to barrel/plunger fit or friction interference.

While a preferred embodiment in accordance with the invention has been shown and described, it is to be clearly understood that the same is susceptible to numerous changes apparent to one of ordinary skill in the art. Therefore, the present invention should not be deemed to be limited to the details shown and described above, and should be considered to include all changes and modifications that come within the scope of the appended claims.

What is claimed is:

1. A tampon assembly comprising:
   an applicator barrel having a forward end and a rear end;
   a tampon pledget adapted to be positioned within said applicator barrel; and
   a plunger adapted to be positioned in said rear end and adapted to expel said tampon pledget from said applicator barrel through said forward end,
   wherein said applicator barrel is formed of a paper based material having an outer surface directly coated with a nitrocellulose layer
   said outer surface having a fingergrip area with a plurality of deformations that rupture the paper based material of said applicator barrel but do not penetrate through said nitrocellulose layer.

2. The tampon assembly of claim 1, wherein said paper based material is selected from the group consisting of paper, paper laminate and cardboard.

3. The tampon assembly of claim 1, wherein said nitrocellulose layer has a component selected from the group consisting of castor oil, synthetic paraffin wax, and a combination thereof.

4. The tampon assembly of claim 1, wherein said nitrocellulose coating has a glossy finish.

5. The tampon assembly of claim 1, wherein said plurality of deformations are arranged in a plurality of spaced rows parallel to an edge of said rear end of the applicator barrel.

6. The tampon assembly of claim 5, wherein said plurality of spaced rows are spaced apart by about 0.25 inches.

7. The tampon assembly of claim 6, wherein said plurality of deformations in each of said plurality of rows are spaced apart by about 0.11 inches.

8. The tampon assembly of claim 5, wherein said plurality of deformations have an average base width from about 0.0045 inches to about 0.080 inches.

9. The tampon assembly of claim 8, wherein said plurality of deformations have an average height about 0.016 inches.

10. The tampon assembly of claim 1, wherein an outer surface of said plunger is provided with a nitrocellulose layer.

11. An applicator barrel for insertion into a body cavity, the applicator barrel being formed of a paper based material, an outer surface of the applicator barrel being directly coated with a nitrocellulose layer, said outer surface being provided with a fingergrip area formed of a plurality of outward extending deformations that rupture the paper based material of said applicator barrel but do not penetrate through said nitrocellulose layer.

12. The applicator barrel of claim 11, wherein said paper based material is selected from the group consisting of paper, paper laminate, and cardboard.

13. A method of forming an applicator barrel having a fingergrip area, said applicator barrel being adapted for insertion into a body cavity, said method comprising:

forming a blank from a paper based material;

coating a first side of said blank with a nitrocellulose coating;

drying said nitrocellulose coating to form a nitrocellulose layer;

winding said blank to form an applicator barrel on which said nitrocellulose layer forms an exterior surface; and piercing said paper based material a plurality of times from inside said barrel through said first side to form a plurality of deformations that rupture the paper based material of said applicator barrel but do not penetrate through the nitrocellulose layer, to form a fingergrip in the fingergrip area.

14. The method of claim 13, wherein said blank is convolutely wound.

15. The method of claim 13, wherein said blank is spirally wound.

16. The method of claim 13, wherein said paper based material is selected from the group consisting of paper, paper laminate, and cardboard.

17. The applicator barrel of claim 13, wherein said plurality of deformations are arranged in a plurality of spaced rows parallel to an edge of a rear end of said applicator barrel.

18. The method of claim 17, wherein said plurality of spaced rows are spaced apart by about 0.25 inches, and the deformations in each of said plurality of rows are spaced apart by about 0.11 inches.

19. The method of claim 17, wherein said plurality of deformations have an average base width about 0.0045 inches to about 0.080 inches, and an average height about 0.016 inches.

* * * * *